United States Patent [19]

Bernstein

[11] Patent Number: 4,933,174

[45] Date of Patent: * Jun. 12, 1990

[54] METHOD OF USING A LIQUID DETERGENT WITH SUNSCREEN AGENT

[75] Inventor: Joel E. Bernstein, Deerfield, Ill.

[73] Assignee: Amethyst Investment Group, Inc., Chicago, Ill.

[ * ] Notice: The portion of the term of this patent subsequent to Oct. 20, 2004 has been disclaimed.

[21] Appl. No.: 109,952

[22] Filed: Oct. 19, 1987

Related U.S. Application Data

[63] Continuation of Ser. No. 601,117, Apr. 18, 1984, Pat. No. 4,701,321, which is a continuation of Ser. No. 375,476, May 6, 1982, abandoned.

[51] Int. Cl.$^5$ .......................... A61K 7/42; A61K 7/44
[52] U.S. Cl. .......................................... 424/60; 424/59
[58] Field of Search ................................... 424/60, 59

[56] References Cited

U.S. PATENT DOCUMENTS

| | | | |
|---|---|---|---|
| 3,152,181 | 1/1961 | Shapiro et al. | 424/60 |
| 3,903,008 | 9/1975 | Deweever et al. | 252/DIG. 5 X |
| 3,941,711 | 3/1976 | Gipson | 252/DIG. 5 X |
| 4,098,881 | 7/1978 | Majeti | 424/59 |
| 4,129,645 | 12/1978 | Barnett et al. | 424/59 |
| 4,256,611 | 3/1981 | Egan et al. | 252/548 |
| 4,335,104 | 6/1982 | VanCleave | 424/59 |
| 4,450,091 | 5/1984 | Schmolka | 424/70 X |
| 4,456,586 | 6/1984 | Vanlerberghe et al. | 424/59 |
| 4,567,038 | 1/1986 | Ciaudelli et al. | 424/59 |
| 4,597,963 | 1/1986 | Deckner | 424/59 |
| 4,666,711 | 5/1987 | Vanlerberghe et al. | 424/59 |

FOREIGN PATENT DOCUMENTS

| | | | |
|---|---|---|---|
| 1070244 | 1/1975 | Canada | 424/59 |
| 2604554 | 11/1977 | Fed. Rep. of Germany | 424/59 |
| WO80/00410 | 3/1980 | PCT Int'l Appl. | 424/59 |

OTHER PUBLICATIONS

Giese et al., J. of the Am. Pharmaceutical Assoc. Scientific, ed., pp. 30–36 (1950).
Balsam et al., Cosmetics: Science and Technology, Wiley, 2nd ed., vol. II, p. 101.
Handbook of Non-Prescription Drugs, Am. Phar. Assoc., 5th ed., 1977, pp. 286–287.
Tamura et al., "Tests for Specific Components in Cosmetics", Chem. Abstracts, vol. 69, No. 109748a (1968).
Happi Household & Personal Products Industry, vol. 18, No. 4, Apr. 1981, p. 48.

*Primary Examiner*—Sam Rosen
*Attorney, Agent, or Firm*—Allegretti & Witcoff, Ltd.

[57] ABSTRACT

A liquid composition comprising a sunscreen agent, a preservative, and a non-ionic detergent, an amphoteric detergent or a mixture thereof in an aqueous vehicle. The sunscreen agent is selected from an aminobenzoic acid, the esters of an aminobenzoic acid, homosalate, cinoxate, and oxybenzone and is present in an amount of not less than about 1 percent by weight of the composition. Applying the composition to the skin leaves an effective amount of the sunscreen agent on the skin even after rinsing to protect the skin against sunburn.

34 Claims, No Drawings

METHOD OF USING A LIQUID DETERGENT WITH SUNSCREEN AGENT

This is a continuation of application Ser. No. 601,117 filed April 18, 1984, now U.S. Pat. No. 4,701,321 which is turn is a continuation of application Ser. No. 375,476, filed May 6, 1982, now abandoned.

BACKGROUND OF THE INVENTION

Exposure to ultra-violet light primarily through exposure to the sun's rays produces a number of harmful effects including premature aging, loss of elasticity, wrinkling, drying, and not least, an increased risk of developing skin cancer. Currently a number of sunscreen and suntan products are marketed to protect against these harmful effects. All of these products contain agents known to filter out some of sun's harmful rays incorporated into creams, ointments, lotions, solutions or suspensions. Such products are applied just prior to anticipated sun exposure and provide short term protection and are removed by bathing, washing or normal desquamation of skin.

I have discovered that such sunscreens can be effectively incorporated into nonionic and amphoteric liquid detergents so that repeated washing and bathing with such detergents leaves a long-lasting substantive and effective amount of the incorporated sunscreen in the stratum corneum of the skin. Previous attempts, including attempts of my own, to incorporate sunscreens into soaps have failed because ionic soaps would rapidly degrade the incorporated sunscreen. The current invention solves this problem by incorporating these sunscreen agents into nonionic or amphoteric detergent vehicles.

SUMMARY

The principal object of the invention is to provide a liquid detergent or soap containing an effective sunscreen agent therein such that washing with these detergents leaves a long-lasting substantive amount of the sunscreen in the stratum corneum of the skin.

It is another object of the present invention to provide a method of controlling the absorption of ultra-violet light by skin exposed to ultra-violet light comprising providing a non-ionic detergent, an amphoteric detergent or mixtures thereof having an effective amount of a sunscreen therein, and periodically applying the same to the skin prior to the exposure of the skin to the ultra-violet light.

Yet another object of the present invention is to provide a method of the type set forth wherein the sunscreen agent in selected from aminobenzoic acids and esters thereof, homosalate, cinoxate, and oxybenzone.

Yet another object of the present invention is to provide a method of controlling the absorption of ultra-violet light by skin exposed to ultra-violet light comprising providing a composition including a sunscreen agent, a preservative, and a non-ionic detergent or a combination of a non-ionic detergent and an amphoteric detergent, the sunscreen agent being selected from the group consisting of aminobenzoic acid, glyceryl p-aminobenzoate, padimate A, padimate O, homosalate, cinoxate, and oxybenzone, the sunscreen agent being present in an amount not less than about 1 percent by weight of the composition, the preservative being present in the range of from 0 to about 0.5 percent by weight of the composition, and periodically applying the composition to the skin prior to exposing the skin to ultra-violet light.

A still further object of the present invention is to provide a sunscreen detergent comprising a non-ionic detergent containing an effective amount of a sunscreen agent therein.

Yet another object of the present invention is to provide a sunscreen detergent comprising a non-ionic detergent or an amphoteric detergent or mixtures thereof containing an effective amount of a sunscreen agent therein.

A final object of the present invention is to provide a sunscreen agent, a preservative, and a non-ionic detergent, an amphoteric detergent or mixtures thereof, the sunscreen agent being selected from the group consisting of aminobenzoic acids and the esters thereof, homosalate, cinoxone and oxybenzone, the sunscreen being present in an amount not less than about 1 percent by weight of the composition, the preservative being present in the range of from about 0 to about 0.5 percent by weight of the composition.

These and other objects of the present invention may be more readily understood when considered in conjunction with the following Examples which are exemplary in nature only.

DETAILED DESCRIPTION OF THE PREFERRED EMBODIMENTS

For the purposes of this application, the term "detergent" is used in its broadest sense to include technical soaps(saponification of fats and oils) as well as synthetic soaps or detergents, many of which are addition products of ethylene oxide and a compound with an active hydrogen atom. The principal requirement of the present invention is that the detergent or the soap be either non-ionic or amphoteric in character. Chemically, a soap may be represent as R-COOM wherein R is a straight chain hydrocarbon radical, either saturated or unsaturated and normally with 7 to 21 carbon atoms. The coo-moiety is the residue of a carbocyclic acid group and is characteristic of natural soaps. M is a base forming material, either inorganic or organic.

As is well known, various animal fats as well as vegetable oils may be used as a constituent in the soap or detergent. One of the preferred vegetable oils is coconut oil which contains a high proportion of saturated fatty acids but has a low average molecular weight, being a liquid at ambient temperature. Olive oil while having a high average molecular weight contains a high proportion of unsaturated fatty acids, also being liquid at ambient temperatures. The invention principally concerns liquid detergents which includes in its definition the aforementioned soaps.

Any well known sunscreening agent may be used; however, the preferred sunscreening agents are listed below. In all cases where weight percents are listed after the sunscreen agent, the lower number in the range is thought to be the least amount of sunscreen effective if used along without additional sunscreening agents while the higher number in the range indicates the maximum amount thought to be economically feasible to put into a liquid detergent. Adding a greater amount of suncreen agent is not deleterious, simply more expensive. However, as the concentration of suncreen agents is increased, less ultra-violet is accepted by the skin resulting in less tanning.

In the practice of this invention sunscreen detergents are prepared by incorporating a variety of chemically dissimilar sunscreen agents into nonionic or amphoteric liquid detergents. The following sunscreen agents were incorporated into various liquid detergent vehicles: amino-benzoic acid, 5–15 percent (all percents provided are calculated as weight/weight); cinoxate (2-ethoxyethyl p-methoxycinnamate), 1–3 percent; digalloyl trioleate, 2–5 percent; 2-ethylhexyl p-methoxycinnamate, 2–5 percent; glyceryl p-aminobenzoate, 2–3 percent; homosalate, 4–15 percent; dioxybenzone, 0.5–5 percent; oxybenzone (2-hydroxy-4-methoxybenzophenone), 0.5–5 percent, padimate A (pentyl p-[p-dimethylamino] benzoate), 1–4 percent, padimate 0 (2-ethylhexyl [p-dimethylamino] benzoate) 1–5 percent. Not all of these agents are equally effective when incorporated into the nonionic or amphoteric liquid detergents nor do all provide equivalent substantivity (long-lastingness). For example, 15 percent homosalate provides far less sun protection than aminobenzoic acid 5 percent after 1,5 and 14 days of washing. However, all the named sunscreen agents do provide substantive ultraviolet protection to some degree.

EXAMPLE 1

A nonionic liquid detergent vehicle was prepared by incorporating into water 5 percent by weight exthoxylated phenols, 1 percent by weight acetylated ethoxylated lanolin. To that was added a sunscreen agent, aminobenzoic acid, in the amount of about 5 percent by weight. The aqueous mixture was used twice daily to cleanse a 25 cm$^2$ square area of skin on the forearm. At the end of ten days the treated area and a 25 cm$^2$ untreated area on the opposite forearm were exposed to a Hanovia quartz lamp at 10 inches distances for 20 minutes. Sunburn erythema was marked in the untreated area 8 hours after exposure, but not observed in the sunscreen detergent washed area.

EXAMPLE 2

A combination nonionic and amphoteric liquid detergent was prepared by adding to water 10 weight percent of a coconut based imidazoline derivative (Miranol), 15 percent by weight cocoamidobetaine, 0.5 percent by weight polysorbate, 0.7 percent by weight of a viscosity adjusting agent quarternary polymer, 0.1 percent by weight methyl paraben as a preservative for the amphoteric detergent. To this mixture was added 1.5 percent aminobenzoic acid. This detergent composition was used daily for two weeks by a 12 year old boy with a sun-sensitive skin prior to swimming in a swimming pool. Although the boy swam and sunbathed for 4 hours, no sunburn erythema developed.

EXAMPLE 3

A nonionic detergent was prepared by adding a 5 percent by weight polysorbate to water and to that was added 1 percent cinoxate as a sunscreen agent. The composition was used for daily washing for 6 weeks by a 37 year old woman. After 4 weeks of use this woman travelled to Florida where she was exposed to significant amounts of sunlight with sunburning.

EXAMPLE 4

An amphoteric liquid detergent was prepared by adding to water 10 percent by weight cocoamidobetaine, 5 percent by weight ammonium lauryl ether sulfate, 0.1 percent by weight propyl paraben as a preservative for the amphoteric detergent and to this was added 2.5 percent by weight glyceryl p-aminobenzoate as a sunscreen agent. This detergent composition was used twice daily to cleanse a 25 cm$^2$ area of skin on the forearm. At the end of 10 days, the treated area and a 25 cm$^2$ untreated area on the opposite arm were exposed to a Hanovia quartz lamp at 10 inches distance for 20 minutes. Sunburn erythema was deep red in the untreated area 8 hours after exposure, but only very faint pink in the treated area.

EXAMPLE 5

A combination nonionic and amphoteric liquid deterent was prepared by adding to water 5 percent by weight ethoxylated phenols, 10 percent by weight coconut based imidazoline derivative (Miranol), and 2 percent by weight sodium lauryl ether sulfate; also added as a preservative was 0.1 percent by weight methyl paraben and 0.1 percent by weight propyl paraben; also added as a viscosity adjusting agent was 0.7 percent quarternary polymer. To this was added 2 percent by weight homosalate. The resulting detergent composition was used to cleanse a 25 cm$^2$ area of the forearm once daily for 4 weeks. At the end of this 4 week period, the treated arm and a 25 cm$^2$ untreated area on the opposite forearm were exposed to a Hanovia quartz lamp at 10 inches distance for 20 minutes. Sunburn erythema was less marked in the detergent washed area 8 hours after exposure than was the untreated area.

EXAMPLE 6

A nonionic liquid detergent comprised of water vehicle having 5 percent by weight polysorbate was used with 2 percent by weight oxybenzone to wash the right forearm of a volunteer subject 12 times in a 6 hour period. The left arm was washed with only the plain nonionic liquid detergent without the oxybenzone. At the end of the 6 hour period both forearms were exposed to 20 minutes U.V. light from a Hanovia quartz lamp at 10 inches distance. The following morning sunburn erythema was observed in the left arm but not in the right arm.

EXAMPLE 7

A nonionic liquid detergent vehicle comprised of water and 2.5 percent by weight polysorbate in water was prepared with 2.5 percent by weight padimate A added as a sunscreen agent. The resulting detergent composition was used as set forth in Example 6 to wash the forearms of a 39 year old man prior to sun exposure. The sunscreen containing nonionic liquid detergent composition provided superior protection from the harmful U.V. rays are compared to the plain nonionic liquid detergent.

EXAMPLE 8

An amphoteric liquid detergent was prepared by adding to water 12 percent by weight of a coconut based imidazoline derivative (Miranol), a 15 percent by weight cocoamidobetaine, a preservative consisting of 0.1 percent by weight methyl paraben and 0.1 percent by weight propyl paraben, a sunscreen agent of padimate O in the amount of 5 percent by weight and a viscosity adjusting agent of quarternary polymer present in the amount of 0.7 percent by weight and 1 percent by weight of an acetylated ethoxylated lanolin. The lanolin was used to provide better cosmetic properties to the composition. The amphoteric liquid detergent composition was used by a 39 year old male to wash twice daily for 14 days which provided noticeable protection from sunburn upon exposure to ultra-violet rays.

It will be seen therefore that there has been provided a plurality of liquid detergent vehicles each provided with an effective sunscreen agent therein. These non-ionic and/or amphoteric vehicles are stable over long periods of time and provide substantive and effective sunscreen agents to the stratum corneum of the skin.

While there has been disclosed what at present is considered to be the preferred embodiments of the present invention, it will be appreciated by those skilled in the art that various modifications and alterations may be made therein without departing from the true spirit and scope of the present invention, and it is intended to cover in the claims appended hereto all such modifications and alterations.

I claim:

1. A method of controlling the absorption of ultraviolet light by skin exposed to ultraviolet light, comprising the steps of: (a) applying to the skin a liquid combination sunscreen detergent that further comprises in combination (i) a liquid detergent component consisting primarily of an aqueous based composition including either a non-ionic detergent or an amphoteric detergent or mixtures thereof, and (ii) an amount of at least one sunscreen agent sufficient to leave an effective amount of said sunscreen on the skin to substantively reduce the absorption of ultraviolet light by said skin so as to provide noticeable protection from sunburn, and (b) rinsing said suncreen detergent from the skin prior to exposure of the skin to the ultraviolet light.

2. The method of claim 1, wherein said non-ionic detergent is an ethoxylated phenol.

3. The method of claim 1, wherein said non-ionic detergent is polysorbate.

4. The method of claim 1, wherein said amphoteric detergent is a vegetable oil based compound.

5. The method of claim 4, wherein said amphoteric detergent is a coconut oil based compound.

6. The method of claim 5, wherein said amphoteric detergent is a coconut based imidazoline compound.

7. The method of claim 1, wherein said amphoteric detergent is a sulfate of a long chain hydrocarbon radical having from 7 to 21 carbon atoms.

8. The method of claim 7, wherein said amphoteric detergent is ammonium lauryl ether sulfate.

9. The method of claim 1, wherein said sunscreen agent includes aminobenzoic acid.

10. The method of claim 1, wherein said sunscreen agent includes an agent selected from the group consisting of aminobenzoic acid, an ester of aminobenzoic acid and mixture thereof.

11. The method of claim 1, wherein said sunscreen agent includes cinoxate.

12. The method of claim 1, wherein said sunscreen agent includes oxybenzone.

13. The method of claim 1, wherein said sunscreen agent is present in an amount not less than about 1 percent by weight of the total amount of detergent.

14. The method of claim 1, wherein said sunscreen agent is present in an amount of between about 1 percent to about 20 percent by weight of the total amount of detergent.

15. The method of claim 1, wherein the detergent also is provided with a preservative and a viscosity adjusting agent.

16. The method of claim 1, wherein said at least one sunscreen agent comprises the combination of two or more sunscreen agents selected from the group consisting of aminobenzoic acid, an ester of aminobenzoic acid, cinoxate, homosalate, oxybenzone, and padimate.

17. The method of claim 1, wherein steps "a" and "b" are repeated at least twelve times.

18. A method of controlling the absorption of ultraviolet light by skin exposed to ultraviolet light, comprising the steps of: (a) applying to the skin a liquid combination sunscreen detergent that further comprises in combination (i) a liquid detergent component consisting primarily of an aqueous based composition including a non-ionic detergent or an amphoteric detergent of mixture thereof, and (ii) an amount of at least one sunscreen agent sufficient to leave an effective amount of said sunscreen on the skin to substantively reduce the absorption of ultraviolet light by said skin so as to provide noticeable protection from sunburn, and (b) rinsing said sunscreen detergent from the skin prior to exposure of the skin to the ultraviolet light, and (c) repeating steps "a" and "b" above for at least 10 days.

19. The method of claim 18, wherein said non-ionic detergent is an ethoxylated phenol.

20. The method of claim 18, wherein said non-ionic detergent is polysorbate.

21. The method of claim 18, wherein said amphoteric detergent is a vegetable oil based compound.

22. The method of claim 21, wherein said amphoteric detergent is a coconut oil based compound.

23. The method of claim 22, wherein said amphoteric detergent is a coconut based imidazoline compound.

24. The method of claim 18, wherein said amphoteric detergent is a sulfate of a long chain hydrocarbon radical having from 7 to 21 carbon atoms.

25. The method of claim 24, wherein said amphoteric detergent is ammonium lauryl ether sulfate.

26. The method of claim 18, wherein said sunscreen agent includes aminobenzoic acid.

27. The method of claim 18, wherein said sunscreen agent includes an agent selected from the group consisting of aminobenzoic acid, an ester of aminobenzoic acid and mixture thereof.

28. The method of claim 18, wherein said sunscreen agent includes cinoxate.

29. The method of claim 18, wherein said sunscreen agent includes oxybenzone.

30. The method of claim 18, wherein said sunscreen agent is present in an amount not less than about 1 percent by weight of the total amount of detergent.

31. The method of claim 18, wherein said sunscreen agent is present in an amount between about 1 percent to about 20 percent by weight of the total amount of detergent.

32. The method of claim 18, wherein the detergent also is provided with a preservative and a viscosity adjusting agent.

33. The method of claim 18, wherein said at least one sunscreen agent comprises the combination of two or more sunscreen agents selected from the group consisting of aminobenzoic acid, an ester of aminobenzoic acid, cinoxate, homosalate, oxybenzone, and padimate.

34. The method of claim 18, wherein steps "a" "b" are repeated at least twelve times.

* * * * *